United States Patent [19]

Prevedello et al.

[11] Patent Number: 5,322,556
[45] Date of Patent: Jun. 21, 1994

[54] PROCESS FOR PREPARING A SULFONATED DISPERSANT FROM PETROLEUM ASPHALT FRACTIONS

[75] Inventors: Aldo Prevedello, Milanese; Edoardo Platone, Asti; Elio Donati, Fano, all of Italy

[73] Assignees: Eniricerche S.p.A.; Snamprogetti S.p.A., both of Milan, Italy

[21] Appl. No.: 28,728

[22] Filed: Mar. 8, 1993

Related U.S. Application Data

[63] Continuation of Ser. No. 626,271, Dec. 12, 1990, abandoned.

[30] Foreign Application Priority Data

Dec. 21, 1989 [IT] Italy ................. 22798 A/89

[51] Int. Cl.$^5$ ............ C09D 195/00; C09D 1/08; C09C 1/28; C09C 1/44
[52] U.S. Cl. ................... 106/275; 106/274; 106/278; 106/668; 106/725; 252/353
[58] Field of Search ......... 106/274, 278, 668, 725, 106/809, 275; 252/353; 562/33

[56] References Cited

U.S. PATENT DOCUMENTS

| | | |
|---|---|---|
| 2,121,845 | 6/1938 | Wernicke ............... 196/40 |
| 2,783,273 | 2/1957 | Verley ................. 260/504 |
| 2,815,370 | 12/1957 | Hutchings et al. ........ 562/33 |
| 3,089,842 | 5/1963 | Stratton ............... 562/33 |
| 3,108,060 | 10/1963 | Matthews, II ........... 208/44 |
| 3,173,800 | 3/1965 | Wilson ................. 106/274 |
| 3,970,690 | 7/1976 | Suzuki et al. .......... 260/505 |
| 4,741,868 | 5/1988 | Rooney et al. .......... 562/33 |

FOREIGN PATENT DOCUMENTS 379749 8/1990 European Pat. Off. .
831100 8/1938 France .

*Primary Examiner*—David Brunsman
*Attorney, Agent, or Firm*—Hedman, Gibson & Costigan

[57] ABSTRACT

A process for preparing a sulfonated dispersant from a petroleum asphalt fraction, comprising:

establishing contact between the asphalt fraction dissolved in an inert solvent and liquid or gaseous sulfur trioxide at a temperature equal to or less than 60° C., to obtain a sulfonated asphalt fraction;

salifying the sulfonated asphalt fraction thus obtained by contact with an aqueous solution of a hydroxide of an alkaline metal, alkaline earth metal or ammonium and recovering the sulfonated salt from the reaction mixture.

This process provides water-soluble sulfonated salts of petroleum asphalt fractions, which can be used as fluidifying and stabilizing agents for aqueous dispersions of solids, such as aqueous dispersions of coal or cement.

20 Claims, No Drawings

PROCESS FOR PREPARING A SULFONATED DISPERSANT FROM PETROLEUM ASPHALT FRACTIONS

This a continuation of application Ser. No. 07/626,271, filed Dec. 12, 1990, now abandoned.

This invention relates to the preparation of a sulfonated dispersant from a petroleum asphalt fraction and its use as a fluidifying and stabilizing agent for dispersions of solids in an aqueous vehicle.

Sulfonated dispersants consisting essentially of salts of aromatic sulfonic acids are known in the art. For example U.S. Pat. No. 3,277,162 describes a dispersant obtained from the products of condensing formaldehyde with naphthalene sulfonic acid. U.S. Pat. No. 3,970,690 and U.S. Pat. No. 4,541,965 describe dispersants obtained from the products of sulfonation of the residues of petroleum fraction steam cracking, conducted at high and low temperature respectively. In U.K. 2,159,536 a sulfonated dispersant is obtained from the products of sulfonation of tars, especially of fossil coal.

The raw materials which are sulphonated to obtain sulphonated dispersants of the known art are however materials which are available only in limited quantities and this constitutes a problem. On the other hand, other fractions such as the asphaltenes are not considered suitable for the preparation of sulfonated dispersants as they are inclined to produce sulfonates which are insoluble in water. See for example P. P. Gurjar and others, in Chem. Ind. Dev. 1977 11 (2) pages 21–23. According to the present invention a simple and convenient process has now been found for sulfonating petroleum asphalt fractions which enables sulfonates to be produced, of which the alkaline, alkaline earth or ammonium salts are at least for the most part soluble in water.

In accordance therewith the present invention provides a process for preparing sulfonated dispersant from a petroleum asphalt fraction, comprising:

establishing contact between an asphalt fraction dissolved in an inert solvent and liquid or gaseous sulfur trioxide at a temperature of between 0° and 60° C. with a weight ratio of sulfur trioxide to the asphalt fraction of between 0.7:1 and 1.2:1, to obtain a sulphonated asphalt fraction;

salifying the sulphonated asphalt fraction thus obtained by contact with an aqueous solution of an alkaline, alkaline earth or ammonium hydroxide and recovering the sulphonated salt from the reaction mixture.

The petroleum asphalt fractions suitable for the purposes of the present invention are the insoluble products, after extraction with propane, of petroleum distillation residues, which typically contain more than 50 wt % of polar components (resins), 10–20 wt % of asphaltenes and 10–20 wt % of aromatics, in addition to small quantities of saturateds, in accordance with ASTM D-2007, or of said insoluble products further extracted with a $C_5$–$C_7$ aliphatic hydrocarbon and consisting essentially of asphaltenes. These asphalt fractions have a number-average molecular weight generally varying from about 600 to about 7000, determined by a vapour pressure osmometer (VPO).

The inert solvents used for dissolving the petroleum asphalt fractions are non-sulfonatable fractions and are conveniently chosen from sulfur dioxide and halogenated and especially chlorinated aliphatic hydrocarbons, such as tetrachloroethylene. According to the process of the present invention the solution of the asphalt fraction in the solvent is brought into contact with liquid or gaseous sulfur trioxide. The reaction is conducted at a temperature within the range of 0°–60° C. and preferably 5°–30° C., with a weight ratio sulfur trioxide to the asphalt fraction of between 0.7:1 and 1.2:1 and preferably between 0.8:1 and 1.1:1. Conveniently, an asphalt fraction concentration in the relative solution is maintained within 1–10 wt % and preferably 2–8 wt %. The mass is kept stirred at atmospheric pressure or at higher than atmospheric pressure if this is required to maintain the reaction mixture in the liquid phase. In the process of the present invention the temperature at which the sulfonation is conducted is particularly critical because of the water solubility characteristics of the final sulfonated salts obtained. In this respect, it has been found that when operating at a temperature exceeding 60° C. the quantity of insoluble product becomes undesirably high, the best results in relation to solubility being obtained by operating between 5° and 30° C. The reaction time required to obtain complete or substantially complete sulfur trioxide conversion varies normally from 1 to 10 hours and is typically of the order of 3 hours. On termination of sulfonation the inert solvent is eliminated and the sulfonated asphalt fraction is neutralized by adding an aqueous solution of a hydroxide of an alkaline metal, alkaline earth metal or ammonium. Sodium hydroxide is preferably used. In practice the hydroxide addition is continued until a pH of the order of 7–10 is obtained.

In particular, if using sulfur dioxide as the reaction solvent, the sulfur dioxide is firstly eliminated and the sulfonated asphalt fraction is neutralized. If the reaction solvent is a chlorinated hydrocarbon the solvent can be eliminated before and/or after neutralization.

By operating in the aforesaid manner an aqueous solution of alkaline metal, alkaline earth metal or ammonium salts of the sulphonated asphalt fraction is obtained substantially free of insoluble material or containing only a small quantity of insoluble material, which is conveniently eliminated for example by filtration or centrifuging.

The sulphonated dispersant obtained in this manner can be used in the form of an aqueous solution, or can be separated by eliminating the water, for example by evaporation or lyophilization. The dispersant obtained by the process of the present invention generally consists of 40–80 wt % of the sulphonated salt of the asphalt fraction, the remainder being the corresponding sulfate salt. The content of this latter can be reduced by known methods such as dialysis and ultrafiltration. The process of the present invention is simple and convenient and enables a water-soluble sulfonated dispersant free of harmful impurities to be obtained from a widely available low-cost raw material. Such a sulfonated product can be used as the dispersant in dispersions of solids in an aqueous vehicle, so reducing the dispersion viscosity or enabling the quantity of dispersed solid to be increased for equal viscosities. In these applications the sulfonated dispersant of the present invention displays excellent fluidifying and stabilizing characteristics. Typical examples of dispersions are aqueous dispersions of coal and cements. In addition the sulphonated asphaltenes can be used in all applications in which a dispersant for an aqueous medium is required, for example in forming aqueous dispersions of phytopharmaceuticals for use in agriculture.

The following experimental examples are provided to better illustrate the invention.

In Examples 1 to 5 the asphalt fraction known as the APA residue of the lubricant base refinery cycle is used. Specifically, the residue of the atmospheric distillation of crude petroleum is distilled under vacuum and the vacuum residue is de-asphalted with propane. The propane-insoluble product constitutes the APA residue, which is subjected to sulfonation. This residue has the following characteristics, determined by CNR rules:

| | |
|---|---|
| penetration: | 10 (tenths of mm) |
| ring-and-ball: | 65° C. |
| penetration index: | −1.12 |
| Fraass brittle-point | +11° C. |
| specific gravity: | 1.052 (at 25° C.) |

Analysis of the APA residue gives the following results:

| | |
|---|---|
| asphaltenes: | 17.1 wt % |
| saturateds: | 2.8 wt % |
| aromatics: | 10.8 wt % |
| polars (resins): | 69.3 wt % |

The analysis is done by firstly separating the asphaltenes with n-heptane and then analyzing the residue in accordance with ASTM D-2007.

The viscosity of the APA residue is 28.2 poises (at 120° C.) and its number-average molecular weight is 940.

This latter is determined using a KNAUER vapour pressure osmometer. This is calibrated using solutions of diphenyl in toluene at four different concentrations operating at 37° C., the molecular weight of the APA residue then being determined dissolved in toluene at three different concentrations.

In Examples 6 to 9 the asphalt fraction obtained from the described APA residue is sulfonated after extraction with pentane. The procedure is as follows. 205 g of APA residue and 8 liters of pentane are fed into a 10 liter flask fitted with a mechanical stirrer bulb condenser and thermometer. The mixture is heated slowly until the pentane boils and this condition is maintained for 4 hours. It is then allowed to cool to ambient temperature and the solid residue is filtered off and washed several times with pentane until the filtrate becomes clear. The solid is dried in a vacuum oven for 3 hours. The asphalt fraction obtained in this manner has a number-average molecular weight of 2169, determined by the above osmometric method.

EXAMPLE 1

55 g of APA residue and 450 g of TCE (tetrachloroethylene) are fed into a 1 liter flask fitted with a mechanical stirrer, a bulb condenser and soda traps at the condenser outlet (to block any escape of sulfur oxides). The flask is cooled with a water and ice bath and 55 g of sulfur trioxide (freshly distilled from oleum) diluted with 110 g of TCE are fed in over a period of 85 minutes. During the sulfur trioxide addition the internal temperature of the flask is maintained at about 5°-7° C. After the addition the cooling bath is removed, the temperature is allowed to rise to ambient (about 22°-24° C.) and the mass kept stirred for a further 3 hours. Nitrogen is then passed through the reaction mixture to eliminate any unreacted sulfur trioxide and the sulphur dioxide formed during the reaction, these being blocked in the soda traps. The TCE is partly eliminated (about 120 g) by filtering the reaction mixture. The remainder is eliminated by evaporation in the form of an azeotrope with water after adding aqueous sodium hydroxide to the crude sulfonation product until a final pH of 8.17 is obtained.

The distillation residue is an aqueous solution of the sodium salt of the sulfonated APA residue containing only traces of insoluble product. This solution is centrifuged, concentrated in a rotary evaporator and dried in a vacuum oven at 80°-90° C. for 3 hours.

108.5 g of a solid product are obtained consisting of 70 wt % of the sodium salt of the sulfonated APA residue, the remainder being essentially sodium sulfate and residual water of crystallization. 11.12 g of sulfur dioxide and only traces of sulfur trioxide are collected in the soda traps.

EXAMPLE 2

The procedure of Example 1 is followed, feeding 44 g of APA residue and 453 g of TCE into the flask. The mixture is cooled to about 5°-6° C. and 33 g of sulfur trioxide diluted with 105 g of TCE are fed in over a period of about 50 minutes. After the addition the internal temperature is allowed to rise from 5°-6° C. to ambient temperature (about 22°-24° C.) and the mixture kept stirred for a further 3 hours.

The reaction mixture is flushed with nitrogen and neutralized with aqueous sodium hydroxide to pH 8.17. An aqueous phase containing the sodium salt of the sulfonated APA residue and an organic phase consisting of TCE containing unaltered APA residue are obtained. The organic phase is separated and the residual TCE is removed from the aqueous phase by azetropic distillation with water. The distillation residue is dried as in Example 1 to obtain 41.1 g of a solid product consisting of 60 wt % of the sodium salt of the sulfonated APA residue, the remainder being essentially sodium sulfate and residual water of crystallization. 4.73 g of sulfur dioxide and only traces of sulfur trioxide are collected in the soda traps. The quantity of unreacted APA residue is 12 g.

EXAMPLE 3

A stainless steel pressure vessel is used fitted with a stirrer and with means for temperature measurement, for feeding the reactants and for discharging the reaction product. 202 g of APA residue and 630 g of sulfur dioxide are fed into the pressure vessel. The pressure vessel is cooled by water circulation to maintain the internal temperature at about 19°-22° C., and 182 g of sulfur trioxide are fed in over a period of about 72 minutes. After the addition the mass is kept stirred at the stated temperature for a further 2 hours.

The sulfur dioxide is then degassed (over about 100 minutes), the pressure vessel is purged with nitrogen and 280 g of 19.6 wt % of aqueous sodium hydroxide added. The aqueous solution is then discharged and a further quantity of aqueous sodium hydroxide added until the pH is about 8. The mass is centrifuged to separate 25 g of an insoluble solid residue, and the filtrate is lyophilized under high vacuum.

In this manner 382.2 g of a solid product are obtained consisting of 68 wt % of the sodium salt of the sulfonated APA residue, the remainder being essentially sodium sulfate.

EXAMPLE 4

The procedure of Example 3 is followed, feeding into the pressure vessel 201 g of APA residue and 655 g of sulfur dioxide. The pressure vessel is cooled by water circulation to maintain the temperature at about 22°-25° C., and 201 g of sulfur trioxide are fed in over a period of about 32 minutes. After the addition the mass is heated to 30° C. minutes and kept stirred at this temperature for a further 150 minutes.

The sulfur dioxide is then degassed, the pressure vessel is purged with nitrogen and 300 g of 19.6 wt % aqueous sodium hydroxide added. The aqueous solution is then discharged and a further quantity of aqueous sodium hydroxide added until the pH is about 8, after which the mixture is filtered to separate 142.8 g of insoluble residue.

The filtrate is concentrated and dried to obtain 325 g of a solid product consisting of 43 wt % of the sodium salt of the sulfonated APA residue, the remainder being essentially sodium sulfate and residual water of crystallization.

EXAMPLE 5 (comparison)

The procedure of Example 3 is followed, feeding into the pressure vessel 132 g of APA residue and 630 g of sulfur dioxide. 132 g of sulfur trioxide are fed in over a period of about 4 minutes and the internal temperature rises to 60°-70° C. After the addition the mass is heated to 80° C. and kept stirred at this temperature for a further 70 minutes.

The sulfur dioxide is then degassed, the pressure vessel is purged with nitrogen and 352 g of 19.6 wt % aqueous sodium hydroxide added. The aqueous solution is then discharged and a further quantity of aqueous sodium hydroxide added until the pH is about 8, after which the mixture is filtered to separate 172 g of insoluble residue.

The filtrate is concentrated and dried to obtain 82.9 g of a solid product consisting of 0.5 wt % of the sodium salt of the sulfonated APA residue, the remainder being essentially sodium sulfate (95 wt %) and residual water of crystallization.

EXAMPLE 6

12 g of asphalt fraction and 243 g of TCE are fed into a 1 liter flask fitted with a mechanical stirrer, dropping funnel and bulb condenser. The flask is cooled to about 5° C. and 12 g of sulfur trioxide diluted with 115 g of TCE are fed in via the dropping funnel over a period of about 30 minutes. During the sulfur trioxide addition the internal temperature in the flask does not exceed 6°-7° C. On termination of the addition the cooling bath is removed and the mixture left to rise to ambient temperature (about 22°-24° C.), the mass then being kept stirred for a further 3 hours. It is then flushed with nitrogen and the reaction mixture filtered to recover 238 g of TCE.

The residue is treated with an aqueous sodium hydroxide solution to pH 8, the remaining TCE is removed by azeotropic distillation with water and the mixture filtered to separate 4.54 g of insoluble residue. The filtrate is concentrated in a rotary evaporator and dried in a vacuum oven.

19.6 g of a solid product are obtained consisting of 60 wt % of the sodium salt of the sulfonated asphalt fraction, the remainder being essentially sodium sulfate and residual water of crystallization.

EXAMPLE 7

14.2 g of asphalt fraction and 300 g of TCE are fed into a 1 liter flask fitted with a mechanical stirrer, dropping funnel and bulb condenser. The flask is cooled to about 5° C. and 9.5 g of sulfur trioxide diluted with 142 g of TCE are fed in via the dropping funnel over a period of about 30 minutes. During the sulfur trioxide addition the internal temperature in the flask does not exceed 6°-7° C. On termination of the addition the cooling bath is removed and the mixture left to rise to ambient temperature (about 22°-24° C.), the mass then being kept stirred for a further 3 hours. About 500 g of water and ice are added, the mixture neutralized with aqueous sodium hydroxide and the TCE is recovered by azeotropic distillation with water and the mixture centrifuged to separate 3.4 g of insoluble residue. The filtrate is concentrated in a rotary evaporator and dried in a vacuum oven.

22.4 g of a solid product are obtained consisting of 55 wt % of the sodium salt of the sulfonated asphalt fraction, the remainder being essentially sodium sulfate and residual water of crystallization.

EXAMPLE 8

12 g of asphalt fraction and 253 g of TCE are fed into a 1 liter flask fitted with a mechanical stirrer, dropping funnel and bulb condenser. The flask is cooled to about 5°-7° C. and 12 g of sulfur trioxide diluted with 97 g of TCE are fed in via the dropping funnel over a period of about 30 minutes. During the sulfur trioxide addition the internal temperature in the flask does not exceed 6°-7° C. On termination of the addition the cooling bath is removed and the mixture left to rise to about 20° C., the mass then being heated to 50° C. and kept stirred at this temperature for a further 3 hours. The reaction mixture is filtered and about 600 g of water are added to the residue, the mixture neutralized with aqueous sodium hydroxide to pH 8.4 and the remaining TCE recovered by azeotropic distillation with water. The mixture is then filtered to separate 7.4 g of insoluble residue. The filtrate is concentrated in a rotary evaporator and dried in a vacuum oven.

15.9 g of a solid product are obtained consisting of 54 wt % of the sodium salt of the sulfonated asphalt fraction, the remainder being essentially sodium sulfate.

EXAMPLE 9 (comparison)

20 g of asphalt fraction and 304 g of TCE are fed into a 1 liter flask fitted with a mechanical stirrer, dropping funnel and bulb condenser. The flask is cooled to about 5°-7° C. and 20.1 g of sulfur trioxide diluted with 156 g of TCE are fed in via the dropping funnel over a period of about 30 minutes. During the sulfur trioxide addition the internal temperature in the flask is maintained at 5°-10° C. On termination of the addition the cooling bath is removed and the temperature allowed to rise to about 20° C., the mass then being heated to the solvent boiling point (about 120° C.) for 60 minutes, cooled and neutralized with aqueous sodium hydroxide to pH 8.5. The mixture obtained in this manner is poured into a separating funnel. Most of the TCE (218 g) is recovered as the organic phase and the remainder of the TCE is recovered from the aqueous phase by azeotropic distillation with water. The distillation residue is filtered to separate 25 g of insoluble residue. The filtrate is concentrated in a rotary evaporator and dried in a vacuum oven to obtain a solid consisting almost entirely of sodium sulfate and its water of crystallization.

EXAMPLE 10

The solid product obtained in Example 4, containing 43 wt % of the sodium salt of the sulfonated APA residue (10 g), is dissolved in water (200 ml) and the solution fed into a SPECTRA POR 3 dialysis membrane. The membrane is immersed in a beaker containing 2 liters of water. It is kept immersed for 24 hours. At the end of this period the solution retained by the membrane is found to have a sodium sulfate content of 3 wt % and contains substantially all the sulfonate, while the solution external to the membrane contains practically only sodium sulfate. The first solution is concentrated firstly under vacuum and then in an oven to recover the solid sulfonate with a low sodium sulfate content.

EXAMPLE 11

The sulfonates obtained in Examples 1 to 4, 6 to 8 and 10 are tested for fluidifying characteristics by measuring the viscosity of concentrated dispersions of coal in water with the sulfonates added.

For this purpose, 35 g of Polish coal dry-ground to a particle size of less than 60 mesh, 0.25 g of sodium sulfonate (the quantity referring to the active part, i.e. excluding the sodium sulfate) and water are fed into a 200 ml beaker to obtain a suspension with the following composition:

| | |
|---|---|
| coal: | 70 wt % |
| sodium sulfonate: | 0.5 wt % |
| water: | 29.5 wt % |

The viscosity measurements are made on the suspensions at various velocity gradients in an RV 12 Haake rotational viscometer. The suspensions are stirred for 1 minute at 650 rpm and for 2 minutes at 1200 rpm using a metal whip stirrer. The thus stirred suspensions are introduced into the Haake viscometer temperature-controlled at 20° C. and the shear force measured at various velocity gradients (maximum 150 sec$^{-1}$). Table 1 shows the apparent viscosity values of the suspensions at 30 and 100 sec$^{-1}$ in mPas. The table also shows the values of K and n obtained by applying to the experimental data the Ostwald equation:

$$\tau = K \cdot \dot{\gamma}^n$$

where
 $\tau$ = shear force (Pa)
 K = consistency index (Pa.sec$^n$)
 $\dot{\gamma}$ = velocity gradient (sec$^{-1}$)
 n = Newtonian index

TABLE 1

| Sulphonate Ex. No. | Apparent viscosity (mPas) | | Ostwald | |
|---|---|---|---|---|
| | 30 sec$^{-1}$ | 100 sec$^{-1}$ | n | K |
| 1 | 519 | 535 | 1.016 | 0.494 |
| 2 | 674 | 651 | 0.953 | 0.800 |
| 3 | 532 | 549 | 1.001 | 0.542 |
| 4 | 740 | 701 | 0.930 | 0.952 |
| 6 | 695 | 656 | 0.943 | 0.852 |
| 7 | 701 | 637 | 0.912 | 0.953 |
| 8 | 960 | 626 | 0.671 | 2.897 |
| 10 | 612 | 611 | 0.996 | 0.620 |

From the data of Table 1 it can be seen that all the sulphonates obtained by the process of the invention are good fluidifiers. The best results are obtained with the sulphonate of Example 3, the suspension of which is practically newtonian at the lower viscosity.

We claim:

1. A process for preparing a sulfonated dispersant from a petroleum asphalt fraction comprising:
   contacting an asphalt fraction comprising more than 50 weight percent of polar compounds, from 10 to 20 weight percent of asphaltenes, from 10 to 20 weight percent of aromatics and small quantities of saturateds dissolved in an inert solvent with liquid or gaseous sulfur trioxide at a temperature of between 0° and 60° C. with a weight ratio of sulfur trioxide to the asphalt fraction of between 0.7:1 and 1.2:1, to obtain a sulfonated asphalt fraction; and
   salifying the sulfonated asphalt fraction by contacting the sulfonated asphalt fraction with an aqueous solution of an alkaline, alkaline earth or ammonium hydroxide and recovering the sulfonated salt from the reaction mixture.

2. A process as claimed in claim 1, wherein the asphalt fraction comprises the insoluble products, after extraction with propane, of petroleum distillation residues.

3. A process as claimed in claim 2 wherein said asphalt fraction comprises the insoluble products after further extraction with a $C_5$-$C_7$ aliphatic hydrocarbon.

4. A process as claimed in claim 2, wherein said asphaltenes consist essentially of asphaltenes having a number-average molecular weight of between about 600 and about 7000, determined by a vapor pressure osmometer.

5. A process as claimed in claim 1, wherein the solvent comprises liquid sulfur dioxide or halogenated aliphatic hydrocarbons.

6. A process as claimed in claim 5 wherein said solvent comprises a chlorinated aliphatic hydrocarbon.

7. A process as claimed in claim 6 wherein said solvent comprises tetrachloroethylene.

8. A process as claimed in claim 1, wherein the sulfonation reaction is conducted at a temperature of between 5° and 30° C., with a weight ratio of sulfur trioxide to the asphalt fraction of between 0.8:1 and 1.1:1, with an asphalt fraction concentration in the reactive solution of from 1-10 wt %, at atmospheric or higher pressure, with a reaction time of between 1 and 10 hours.

9. A process as claimed in claim 8 wherein the sulfonation reaction is carried out with an asphalt fraction concentration in the reactive solution of from 2 to 8 weight percent.

10. A process as claimed in claim 8 wherein the sulfonation reaction is carried out for a reaction time of about 3 hours.

11. A process as claimed in claim 1, wherein the sulfonated asphalt fraction is contacted with an aqueous solution of a hydroxide of an alkaline metal, alkaline earth metal or ammonium, to obtain a pH of from 7-10.

12. A process as claimed in claim 11 wherein said aqueous solution of a hydroxide comprises an aqueous solution of sodium hydroxide.

13. A process as claimed in claim 1, wherein sulfur dioxide is used as the solvent for the asphalt fraction, and wherein said sulfur dioxide is eliminated at the end of the sulfonation reaction before salifying the sulfonated asphalt fraction.

14. A process as claimed in claim 1, wherein said solvent for the asphalt fraction comprises a halogenated aliphatic hydrocarbon, said halogenated aliphatic hydrocarbon being eliminated at the end of the sulfonation reaction before and/or after salifying the sulfonated asphalt fraction.

15. A method of fluidifying and stabilizing an aqueous dispersion of solids comprising adding to the aqueous dispersion of solids an effective amount of the sulfonated dispersant produced by the process as defined in claim 1.

16. A method as claimed in claim 15, wherein said aqueous dispersions are aqueous dispersions of coal or cement.

17. A process for preparing a fluid dispersion of solids in water comprising adding said solids to the water in the presence of a dispersant prepared by a process comprising the steps of:

contacting an asphalt fraction comprising more than 50 weight percent of polar compounds, from 10 to 20 weight percent of asphaltenes, from 10 to 20 weight percent of aromatics and small quantities of saturateds dissolved in an inert solvent with liquid or gaseous sulfur trioxide at a temperature of between 0° and 60° C. with a weight ratio of sulfur trioxide to the asphalt fraction of between 0.7:1 and 1.2:1, to obtain a sulfonated asphalt fraction; and salifying the sulfonated asphalt fraction by contacting the sulfonated asphalt fraction with an aqueous solution of an alkaline, alkaline earth or ammonium hydroxide and recovering the sulfonated salt from the reaction mixture.

18. A process for preparing a fluid dispersion as defined in claim 17 wherein said solids comprise coal or cement.

19. A process for preparing a fluid dispersion of solids in water comprising adding said solids to the water in the presence of a dispersant prepared by a process comprising the steps of:

contacting a petroleum fraction comprising of petroleum distillation residues extracted with a $C_5$–$C_7$ aliphatic hydrocarbon and consisting essentially of ashpaltenes and having a number-average molecular weight of between about 600 and 7000, determined by vapor pressure osmometer, with liquid or gaseous sulfur trioxide at a temperature of between 0° and 60° C. with a weight ratio of sulfur trioxide to the petroleum fraction of between 0.7:1 and 1.2:1, to obtain a sulfonated petroleum fraction; and salifying the sulfonated petroleum fraction by contacting the sulfonated petroleum fraction with an aqueous solution of an alkaline, alkaline earth or ammonium hydroxide and recovering the sulfonated salt from the reaction mixture.

20. A process for preparing a fluid dispersion as defined in claim 19 wherein said solids comprise coal or cement.

* * * * *